US009546990B2

(12) United States Patent
Van Der Goot et al.

(10) Patent No.: US 9,546,990 B2
(45) Date of Patent: Jan. 17, 2017

(54) METHOD FOR THE DETECTION OF EGG YOLK

(75) Inventors: Eddy Alfred Herre Van Der Goot, Barneveld (NL); Rudolf Johan Veeneman, Barneveld (NL)

(73) Assignee: MOBA GROUP B.V., Barneveld (NL)

( * ) Notice: Subject to any disclaimer, the term of this patent is extended or adjusted under 35 U.S.C. 154(b) by 361 days.

(21) Appl. No.: 14/235,845

(22) PCT Filed: Jul. 25, 2012

(86) PCT No.: PCT/NL2012/050532
§ 371 (c)(1),
(2), (4) Date: Apr. 14, 2014

(87) PCT Pub. No.: WO2013/019108
PCT Pub. Date: Feb. 7, 2013

(65) Prior Publication Data
US 2014/0226871 A1      Aug. 14, 2014

Related U.S. Application Data

(60) Provisional application No. 61/512,942, filed on Jul. 29, 2011.

(30) Foreign Application Priority Data

Jul. 29, 2011    (EP) .................................... 11006256

(51) Int. Cl.
*G01N 33/08* (2006.01)
*G06T 7/00* (2006.01)
(Continued)

(52) U.S. Cl.
CPC ............. *G01N 33/08* (2013.01); *A47J 43/145* (2013.01); *G01N 21/8851* (2013.01);
(Continued)

(58) Field of Classification Search
CPC .. G01N 33/08; G01N 33/085; G06K 2209/17; G06T 2207/30128; A23L 1/32; A23V 2250/2044
(Continued)

(56) References Cited

U.S. PATENT DOCUMENTS 3,977,106 A * 8/1976 Kapp ...................... G09F 11/04
283/99
4,591,723 A * 5/1986 Akiyama ............. G01N 21/314
250/461.1
(Continued)

FOREIGN PATENT DOCUMENTS

| EP | 1 297 769 | 4/2003 | |
| IT | WO 2007129349 A1 * | 11/2007 | ............... A23L 1/32 |
| WO | WO 2007/129349 | 11/2007 | |

OTHER PUBLICATIONS

J. Blankestijn, "Effective Cleaning of Stainless Steel Surfaces", 2 pages, TNO innovation for life, http://www.tno.nl/content.cfm?content=prop_case&laag1=laag2=90 . . . Jul. 24, 2012.
(Continued)

*Primary Examiner* — Michael A Newman
(74) *Attorney, Agent, or Firm* — Marvin Petry; Stites & Harbison, PLLC

(57) ABSTRACT

The present invention relates to a method for the detection of egg yolk in albumen, for example, but not exclusively, at least one yolk spot, comprising, —breaking an egg, —separating albumen and yolk, —collecting albumen and yolk separately in a yolk cup and in an albumen cup, —imaging of the albumen cup substantially from above with a camera, whereby an albumen image is obtained, and —imaging, substantially from above, of the yolk cup, having yolk area Ay, a preselected subarea Py, whereby a yolk image in a preselected color system Sy is obtained.

8 Claims, 2 Drawing Sheets

Figure 1:
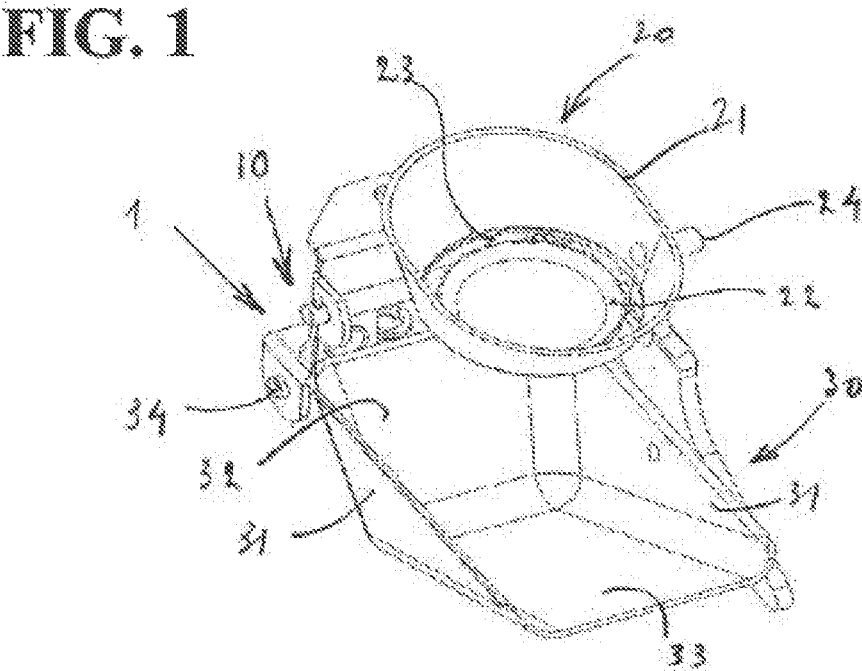

(51) Int. Cl.
*A47J 43/14* (2006.01)
*G01N 21/88* (2006.01)

(52) U.S. Cl.
CPC .......... *G06T 7/004* (2013.01); *G06K 2209/17* (2013.01); *G06T 2207/30128* (2013.01)

(58) Field of Classification Search
USPC ....................................................... 382/110
See application file for complete search history.

(56) References Cited

U.S. PATENT DOCUMENTS

| | | | | |
|---|---|---|---|---|
| 4,622,469 | A * | 11/1986 | Akiyama | G01N 21/6486 250/458.1 |
| 5,293,815 | A | 3/1994 | Tomosue | |
| 5,858,434 | A * | 1/1999 | Thomas | A47J 43/145 426/299 |
| 2007/0202223 | A1 * | 8/2007 | Oren | G01N 33/08 426/231 |
| 2008/0292758 | A1 | 11/2008 | Kristensen et al. | |

OTHER PUBLICATIONS

International Search Report for PCT/NL2012/050532 dated Mar. 22, 2013.

\* cited by examiner

METHOD FOR THE DETECTION OF EGG YOLK

The present invention relates to a method for detecting egg yolk in albumen, for example, but not exclusively, at least one yolk spot, comprising:
breaking an egg,
separating albumen and yolk,
collecting albumen and yolk separately in a yolk cup and in an albumen cup,
imaging the albumen cup substantially from above with a camera, whereby an albumen image is obtained; and
delivering a characteristic of the albumen image.

Breaking eggs and collecting the yolk and albumen separately on an industrial scale, with so-called egg breakers, is generally known. More particularly, it is known to perform an inspection after collection, to check whether any yolk has ended up in the albumen, and also to clean the respective parts after every breaking operation. Usually, the parts for breaking the eggs on the one hand, and for collecting the yolk and the albumen on the other, are made of stainless steel. In order for these parts—i.e., the claws for holding the egg prior to breaking and holding the eggshell halves after breaking, the breaking knife, the yolk cup for collecting the yolk, most often intact, after breaking, and the albumen cup for collecting as much albumen as possible —to be cleaned as well as possible, this steel is polished electrolytically. In the usual cyclic cleaning, these polished surfaces immediately give away whether any residues are left behind. In, for instance, U.S. Pat. No. 5,293,815, cups of stainless steel with a properly selected composition are noted to have the advantage of good cleanability. In "EFFECTIVE CLEANING OF STAINLESS STEEL SURFACES", see the TNO website, parts of machines for processing food and food components that are made of electrolytically polished stainless steel are mentioned, and are noted as being very properly cleanable.

Although polished steel is highly suitable for such machines, it can reflect in a disadvantageous manner, in particular when applying vision technology. This vision technology is described, for instance, in WO2007129349, where residues of yolk in albumen in collecting trays are observed. Also when using such vision technology in egg breakers with endless conveyors with cups for albumen and yolk, camera systems are used to make images of each consecutive albumen-yolk cup combination or breaker cup unit. With this, possible residues of yolk in the albumen can be traced. Exposure and imaging are such that with a cup of such polished steel, reflection will occur. As is known in this field of food processing technology, this often leads to incorrect characterisation of such cups. More particularly, this means that the albumen cups may provide an image as if yolk residues were present. Upon assessment, such cups are rejected and are therefore known as "false rejects".

In order to remedy this drawback of reflection, the method according to the present invention is characterized by the features of claim 1.

With great advantage, existing cups and manner of manufacturing same can be maintained, while the recognition of yolk in albumen is improved considerably. In particular, an improvement means that fewer so-called "false rejects" occur. With great advantage, the correct determinations of yellow can be performed in the albumen cup too. More particularly, the features according to the invention enable a better recognition of reflections of the steel having colour properties that deviate from the desired colour detection, so that manually normally approved cups are not afterwards rejected, still, through such vision technology. In the albumen cup too, the correct determinations of yellow are now suitably performed.

In a further embodiment of this invention, the method has one or more of the following features:
that for the preselected subarea of the albumen cup it holds that $Pa/Aa \geq 0.80$;
that further, for the yolk spot Aya, a size is determined,
that further still, in the characteristic, Aya/Pa is comprised,
that surfaces of the areas are measured in pixels or derivatives thereof.

The invention further comprises a method for breaking eggs, at least comprising examining and selecting albumen after breaking, wherein a method for detection according to any one of the preceding claims is used.

Several settings and possibilities can thus be suitably set so that the yield can be further improved and enhanced.

Figure 2:
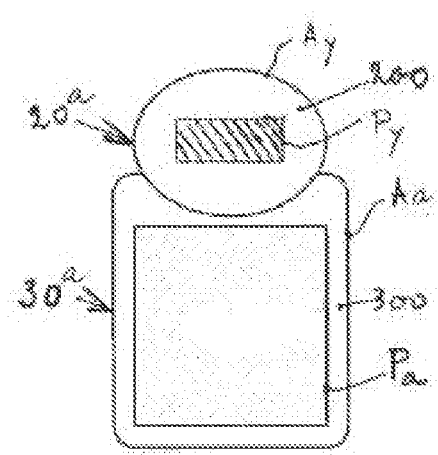
Figure 3:
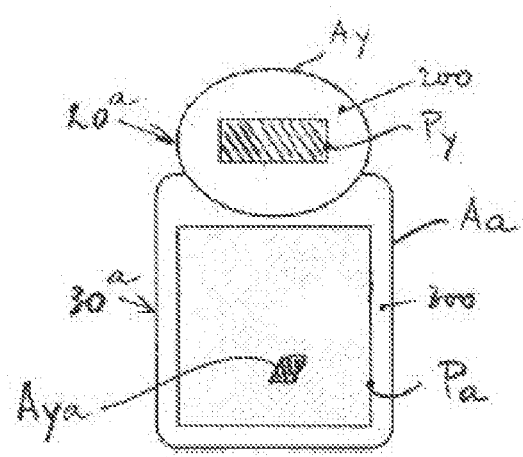
Figure 4:
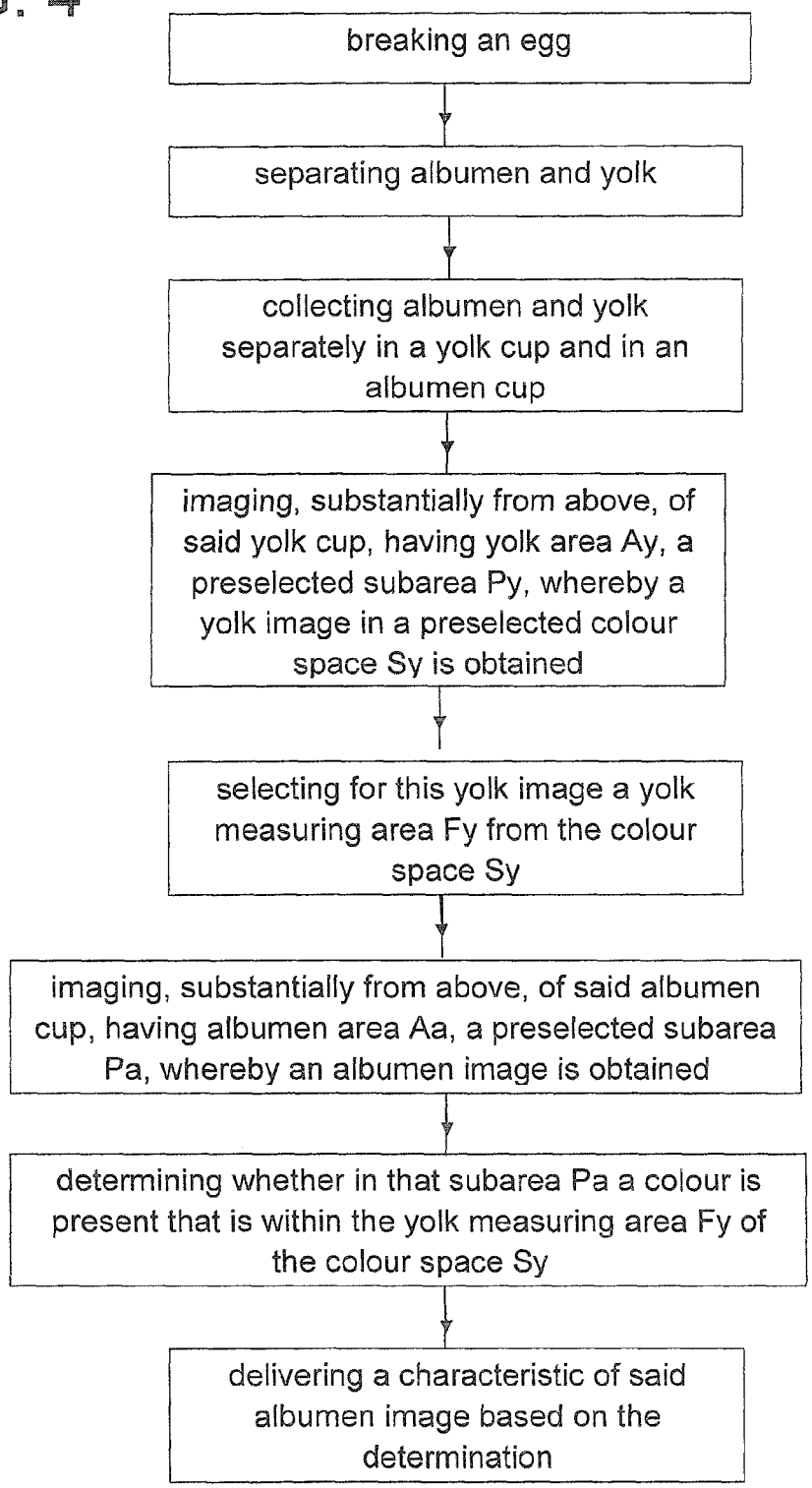

In the following, the method according to the invention will be elucidated in detail with reference to a drawing, in which:

FIG. 1 gives a schematic view obliquely from above of a widely used breaker cup unit, in perspective drawing, FIG. 2 schematically gives a first example of a diagram as represented on a display in which features of an exemplary embodiment according to the invention are recognizable, FIG. 3 schematically gives a second example of a diagram similar to the one of FIG. 2; and FIG. 4 a flow-chart of an embodiment of a method for the detection of egg yolk in albumen.

In the different Figures, the same parts have the same marks and reference numerals.

The Figures show a non-limiting example of a method according to one aspect of the invention, the method comprising the following steps:
breaking an egg (not represented as such);
separating albumen 300 and yolk 200;
collecting the albumen 300 and the yolk 200 separately in a yolk cup 20 and an albumen cup 30;
imaging substantially from above a preselected subarea Py of the yolk cup 20 (filled with yolk 200), whereby a yolk image in a preselected colour space Sy is obtained;
selecting for the obtained yolk image a yolk measuring area Fy from the colour space Sy, the yolk measuring area Fy in particular forming a boundary for specific yellow tones observed in the obtained yolk image;
imaging substantially from above a preselected subarea Pa of the albumen cup 30 (filled with albumen 300), whereby an albumen image is obtained;
while utilizing the yolk measuring area Fy, viewing the subarea Pa of the albumen cup 30, to determine whether in that subarea Pa a colour is present that is within the yolk measuring area Fy; and
delivering a characteristic of the albumen image based on the determination.

In particular, FIG. 1 shows an albumen-yolk cup combination or breaker cup unit 1 represented obliquely from above, with a yolk cup 20 and an albumen cup 30. Such units 1 are connected in rows by a coupling 10 to an endless conveyor, for example, as elucidated in U.S. Pat. No. 5,293,815. Such a yolk cup 20 has substantially the circumferential shape of the lower half of a sphere, with a yolk cup wall 21 extending partly all around, a yolk cup bottom 22 at the underside and, over a part therebetween, a yolk cup slot 23. To this yolk cup 20 is further connected a yolk cup tilting pin 24 with which this cup 20 can be slightly tilted to allow all yolk to flow out into a further yolk collection tray.

Albumen cup 30 comprises sidewalls 31, a first bottom part 32, and a second bottom part 33. To such an albumen cup 30 is connected an albumen cup tilting pin 34, with which this cup 40 can be slightly tilted to allow all albumen to flow out into a further albumen collection tray.

In FIGS. 2 and 3, schematically, diagrams are shown which illustrate the method according to the present invention. These diagrams can be considered as top plan views of the above-discussed breaker cup unit 1, a yolk cup contour 20a, and an albumen cup contour 30a. With such an egg breaker in operation, such contours will be visualized on a display to enable monitoring of the reception and collection of the albumen and the yolk in each successive breaker cup unit 1. In general, these contours 20a, 30a will also be the contours within which all yolk and all albumen are present. The yolk area is indicated with Ay, the albumen area with Aa. Inside these, yolk 200 and albumen 300 are schematically indicated.

More particularly, in FIG. 2, the areas Ay, Aa are indicated for the whole yolk cup and the whole albumen cup, respectively, as well as further respective subareas Py, Pa. As follows from the drawing, Py is a subarea of the yolk cup area Ay. As further follows from the drawing, Pa is a subarea of the albumen cup area Aa. The selection of these areas can be set, for instance, via a control system, for instance, when observing and scanning with a camera.

The colours are measured in a so-called colour space, for example, but not exclusively, in the colour triangle known to anyone skilled in the art, or the range on the Roche scale, or the YUV space or the HSL-HSV coordinate system. It will further be clear to anyone skilled in the art that further possibilities, derivatives or combinations can be selected for this process.

In the present application a choice has been made,
for SY, the yolk colour area, as a denotation of the colour space, in which the yellow of the yolk cup is measured, and
for Fy, the yolk measuring area, as a denotation of that part of this colour space, also referred to as "figure", that forms the boundary for the specific yellow tones which are observed in the case of a specific yolk cup. Fy can also be called a yolk filter or filter.

In this FIG. 2, subarea Py is hatched to thus indicate that yolk is involved. Its colour is measured in the colour space Sy mentioned. Then, a specific part in the colour space Sy is selected, i.e., the above-mentioned yolk measuring area Fy, which can thus be regarded as a yolk filter or filter. With this filter Fy, the subarea Pa in the albumen cup (filled with albumen 300 during use) is observed. As can be seen in this FIG. 2, a hatching as in subarea Py is not in evidence, which means, therefore, that in the albumen, more particularly in the subarea Pa, no yolk has been found.

It is further clear that in the albumen cup contour 30a, the subarea Py forms a part of the whole area Aa. As the yolk will end up in the albumen virtually exclusively above the second bottom part 33, and a camera will depict especially that part of the cup, the subarea Pa is defined especially above that bottom part. To maximize the chance of discovery, according to a preferred embodiment, Pa/Aa≥0.80 is selected. Here, Pa/Aa is for instance a surface ratio of the respective areas. As mentioned, the surfaces of the areas can be measured for instance in pixels or derivatives thereof.

In FIG. 3, a similar view is shown. Unlike in FIG. 2, here, in subarea Pa a yolk residue Aya is represented, the yolk residue forming an assembly of pixels with a colour which is made visible via the above-mentioned filter action in Fy, and which, in other words, has a colour located in the yolk measuring area Fy. Based on this comparison, a choice as indicated hereinabove is made, i.e., "SUITABLE" or "NOT SUITABLE" for further processing, which means
make further use of each of the cup liquids, or
make further use of one of the two, or
make no further use of either of the two.

In this manner, the earlier-mentioned yolk properties are established. More particularly, the colour properties are determined in one of the above-mentioned colour spaces Sy.

In a further embodiment, also the size of yolk spot Aya, as a measure of the amount, can play a part in such decision. The characteristic mentioned can for instance comprise Aya/Pa (in particular the surface ratio between the surface of the spot Aya and the surface of the subarea Pa).

It will be clear to anyone skilled in the art that the surface determinations, or derivatives thereof, can be carried out in the manner common in current vision technology, in pixels, or derived quantities and dimensions.

Through the use of highly specific filters, i.e., the measuring areas Fy mentioned, adjacent colours which can be the result of reflections are recognized and filtered. It has appeared that precisely when using such stainless steel polished cups, the result in collecting especially albumen improves considerably.

With the above-described manner of detection, very large series of egg breaker cup units can be scanned and monitored, and the obtained characteristics can be processed and further processed automatically, with for instance a central processing unit. In the technology of egg breakers, this is of great advantage for determining grand totals, such as yields, as well as for obtaining overviews of the egg feed.

It will be clear to anyone skilled in the art that the invention is not limited to the embodiments described. Various modifications are possible within the framework of the invention as set forth in the appended claims.

| 1 | breaker cup unit | 200 | yolk |
|---|---|---|---|
| 10 | coupling | 300 | albumen |
| 20 | yolk cup | Aa | albumen area |
| 21 | yolk cup wall | Ay | yolk area |
| 22 | yolk cup slot | Pa | preselected albumen subarea |
| 23 | yolk cup bottom | Py | preselected yolk subarea |
| 24 | yolk cup tilting pin | Aya | yolk spot in albumen subarea |
| 30 | albumen cup | Sy | colour space |
| 31 | albumen cup edge | Fy | yolk measuring area, yolk filter, filter |
| 32 | first bottom part | 20a | yolk cup contour |
| 33 | second bottom part | 30a | albumen cup contour |
| 34 | albumen cup tilting pin | | |

The invention claimed is:

1. A method for the detection of egg yolk in albumen, for example, but not exclusively, at least one yolk spot Aya, comprising,
breaking an egg,
separating albumen and yolk,
collecting albumen and yolk separately in a yolk cup and in an albumen cup,
imaging, substantially from above, of said yolk cup, having yolk area Ay, a preselected subarea Py, whereby a yolk image in a preselected colour space Sy is obtained,
selecting for this yolk image a yolk measuring area Fy from the colour space Sy,
imaging, substantially from above, of said albumen cup, having albumen area Aa, a preselected subarea Pa, whereby an albumen image is obtained, determining whether in that subarea Pa a colour is present that is within the yolk measuring area Fy of the colour space Sy, and delivering a characteristic of said albumen image based on the determination.

2. A method according to claim 1, wherein a ratio of the preselected subarea Pa of said albumen cup and the area Aa of the whole albumen cup, Pa/Aa, is selected to be ≥0.80.

3. A method according to claim 1, wherein the method is a method for detecting at least one yolk spot Aya in the albumen, wherein for the yolk spot Aya a size is determined, and that further, in the characteristic, Aya/Pa is comprised, being the surface ratio between the surface of the spot Aya and the surface of the subarea Pa.

4. A method according to claim 1, wherein surfaces of said areas (Aya, Pa) are measured in pixels or derivatives thereof.

5. A method according to claim 1, wherein the albumen cup is manufactured from polished steel.

6. A method for breaking eggs, at least comprising inspecting and selecting albumen after breaking, wherein a method for detection is used according to claim 1.

7. A method according to claim 1, wherein the yolk measuring area Fy forms a boundary for specific yellow tones observed in the obtained yolk image.

8. A method according to claim 1, wherein the colour space is one of: the colour triangle, the range on the Roche scale, or the YUV space or the HSL-HSV coordinate system.

* * * * *